United States Patent
Zhu et al.

[11] Patent Number: 5,941,903
[45] Date of Patent: Aug. 24, 1999

[54] PACEMAKER FOR DETECTION OF EVOKED RESPONSE

[75] Inventors: Qingsheng Zhu, Little Canada; Michael Lyden, Shoreview; Scot Boon, Lino Lakes; Mark Gryzwa, Woodbury, all of Minn.

[73] Assignee: Cardiac Pacemakers, Inc, St. Paul, Minn.

[21] Appl. No.: 09/070,158

[22] Filed: Apr. 30, 1998

[51] Int. Cl.[6] .................................................. A61N 1/37
[52] U.S. Cl. ............................................................ 607/13
[58] Field of Search ................................... 607/9, 13, 28

[56] References Cited

U.S. PATENT DOCUMENTS

| | | |
|---|---|---|
| 3,835,865 | 9/1974 | Bowers ........................................ 607/13 |
| 4,114,627 | 9/1978 | Lewyn et al. . |
| 4,373,531 | 2/1983 | Wittkampf et al. . |
| 4,399,818 | 8/1983 | Money . |
| 4,436,093 | 3/1984 | Belt . |
| 4,498,478 | 2/1985 | Bourgeois . |
| 4,537,201 | 8/1985 | Delle-Vedove et al. . |
| 4,674,508 | 6/1987 | DeCote . |
| 4,686,988 | 8/1987 | Sholder . |
| 4,821,724 | 4/1989 | Whigham et al. . |
| 4,858,610 | 8/1989 | Callaghan et al. . |
| 5,324,310 | 6/1994 | Greeninger et al. ........................ 607/28 |
| 5,443,485 | 8/1995 | Housworth et al. ........................ 607/28 |
| 5,486,201 | 1/1996 | Canfield ...................................... 607/13 |
| 5,571,144 | 11/1996 | Schroeppel ................................. 607/28 |
| 5,601,615 | 2/1997 | Markowitz et al. ........................ 607/28 |
| 5,609,611 | 3/1997 | Bolz et al. .................................. 607/13 |
| 5,658,317 | 8/1997 | Haefner et al. ............................... 607/5 |

*Primary Examiner*—Scott M. Getzow
*Attorney, Agent, or Firm*—Nikolai, Merserau & Dietz P.A.

[57] ABSTRACT

A method and apparatus for attenuating polarization voltages or "afterpotentials" which develop at the heart tissue/electrode interface following the delivery of a pacing stimulus to the heart tissue such that the evoked response of the heart may be accurately detected to determine whether each pacing stimulus resulted in heart capture or contraction, thereby facilitating improved tracking of the capture threshold for minimizing power consumption while assuring therapeutic efficacy. The conventional large capacitance coupling capacitor used to suppress DC components of the pacing pulse is reduced to effectively lower the equivalent capacitance of the pacing and coupling capacitors following delivery of the pacing pulse, allowing shorter recharge and blanking intervals. As a result, the evoked response is more easily detected.

12 Claims, 2 Drawing Sheets

PACEMAKER FOR DETECTION OF EVOKED RESPONSE

BACKGROUND OF THE INVENTION

I. Field of the Invention

The present invention relates generally to implantable and external cardiac rhythm management devices, and more particularly relates to a method and apparatus for attenuating polarization voltages or "afterpotentials" which develop at the lead's electrodes following the delivery of a stimulus to the heart tissue from a pulse generator of the cardiac rhythm management device. The reduction in the effects of afterpotentials enhances the ability to determine whether the stimulus evokes a response in the heart or results in heart capture or contraction while utilizing electrodes for both pacing and sensing, and thereby facilitates improved tracking of the capture threshold for minimizing power consumption while assuring therapeutic efficacy.

II. Discussion of the Prior Art

Cardiac rhythm management devices have enjoyed widespread use and popularity through time as a means for supplanting some or all of an abnormal heart's natural pacing functions. Among the various heart abnormalities remedied by pacemakers include total or partial heart block, arrhythmias, myocardial infarctions, congestive heart failure, congenital heart disorders, and various other rhythm disturbances within the heart. The fundamental components of a cardiac pacemaker include an electronic pulse generator for delivering stimulus pulses to the heart and an electrode lead arrangement (unipolar or bipolar) for sensing evoked responses and intrinsic events from the heart.

Depending upon the heart abnormality, cardiac pacemakers may be designed to engage in ventricular pacing, atrial pacing, or dual chamber pacing in both the atrium and ventricle. Regardless of the type of cardiac pacemaker employed to restore the heart's natural rhythm, all operate to stimulate heart tissue cells adjacent to the electrode of the pacing lead which is employed in the heart and electrically coupled to the pacemaker. When the stimulus evokes a response in the heart, this response is typically referred to as "capture" and is a function of the positive and negative charges found in each myocardial cell within the heart.

More specifically, when a stimulus that evokes a response is applied to the cell membrane, the selective permeability of the cell membrane is disturbed such that it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibril of the cell membrane. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is repolarized with a negative charge within the cell membrane. This causes the cell membrane to relax and return to the fully extended state, referred to as diastole.

Once in diastole, the success of a cardiac pacemaker in depolarizing or "capturing" the heart hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result. Changes in the capture threshold may be detected by monitoring the efficacy of stimulating pulses at a given energy level.

The ability to detect capture in a pacemaker is extremely desirable in that delivering stimulation pulses having energy far in excess of the patient's capture threshold is wasteful of the pacemaker's limited power supply. In order to minimize current drain on the power supply, it is desirable to automatically adjust the pacemaker such that the amount of stimulation energy delivered to the myocardium is maintained at the lowest level that will reliably capture the heart. To accomplish this, a process known as "capture verification" must be performed wherein the pacemaker monitors to determine whether an evoked depolarization or R-wave occurs in the heart following the delivery of each pacing stimulus pulse.

The conventional pacemaker typically includes a pacing output circuit designed to selectively generate and deliver stimulus pulses through a lead to one or more electrodes positioned in the heart of a patient. The pacing output circuit includes a power supply, switches, a pacing charge storage capacitor, and a coupling capacitor, all of which cooperatively operate under the direction of a microprocessor-based controller to perform a charging cycle, a pacing cycle, and a recharging cycle. The capacitance of the pacing charge storage capacitor typically ranges between 10–30 microfarads so as to develop a sufficient pacing charge for stimulating the heart ranges. The capacitance of the coupling capacitor typically ranges between 15 to 40 microfarads with 33 microfarads being typical. A capacitor having a capacitance in this range was believed necessary to deliver sufficient energy to the heart.

The charging cycle involves manipulation of the switches such that the pacing charge storage capacitor is charged up to a predetermined voltage level. The pacing cycle involves manipulating the switches such that the voltage within the pacing charge storage capacitor may be discharged through the coupling capacitor to the electrodes of the pacemaker. The recharging cycle involves further manipulation of the switches for a predetermined period of time following the pacing pulse to allow the coupling capacitor to be discharged.

While the conventional pacing circuit is generally effective in delivering stimulus pulses to the heart, it has been found that the detection of evoked depolarization or "capture verification" is rendered very difficult due to polarization voltages or "afterpotentials" which develop at the heart tissue/electrode interface following the application of the stimulation pulses. The inventors in the present application have discovered that these polarization voltages are due, in large part, to the relatively large capacitance of the conventional coupling capacitor. In the past, the large capacitance of coupling capacitor was believed necessary in order to sufficiently block any DC components from the heart and to minimize pace pulse voltage droop. However, the large capacitance of the coupling capacitor causes a charge dissipation or "afterpotential" which is relatively large (100 mV or greater) and which decays exponentially over a relatively long period of time (100 milliseconds). This is particularly troublesome due to the fact that the evoked potential or R-wave of the heart tissue is small in amplitude (5–20 mV) relative to the polarization voltage or "afterpotential" (100 mV). Moreover, the long decay period of the polarization voltage or "afterpotential" effectively masks the evoked potential or R-wave, which typically begins within approximately (10–20) milliseconds after the stimulation pulse. It will be appreciated that this creates difficulty in detecting the evoked response or R-wave of the heart following the delivery of stimulus pulses. In that evoked response is indicative of capture, the undesirable masking of the evoked response by "afterpotentials" thus hampers the ability of the pacemaker to conduct automatic capture verification. Hence, there is a need for a pacing output circuit that shortens the pacing afterpotentials with minimal increase of the leading edge voltage pacing threshold.

The prior art is replete with patents which address the problem of polarization voltage or "afterpotentials" hindering capture verification in cardiac pacing systems. U.S. Pat. No. 4,373,531 to Wittkampf et al. teaches the use of pre and post stimulation recharge pulses to neutralize the polarization on the pacing lead. U.S. Pat. No. 4,674,508 to DeCote, Jr. teaches the use of paired pacing pulses wherein the waveforms sensed through the pacing lead following the generation of each of the pair of pulses are electronically subtracted to yield a difference signal indicative of the evoked cardiac response. The approaches of the '531 patent and the '508 patent are unnecessarily wasteful of battery power and unduly complex due to the need to deliver opposite-polarity charges and pairs of closely spaced pacing pulses, respectively, to the electrode.

U.S. Pat. No. 4,399,818 to Money teaches the use of a direct-coupled output stage wherein polarization voltages at the heart tissue/electrode interface are dissipated, by shorting the electrodes together. U.S. Pat. No. 4,498,478 to Bourgeois teaches the use of a resistor across the output terminals (electrodes) such that a current path is provided for discharging and recharging the effective capacitance at the electrode/tissue interface. U.S. Pat. 4,537,201 to Delle-Vedove et al. teaches a linearization of the exponentially decaying sensed signal by applying the sensed signal through an anti-logarithmic amplifier in order to detect a remaining nonlinear component caused by the evoked potential. The approach of the '201 patent is disadvantageous in that it requires unnecessarily complex circuitry that is difficult to implement to produce the anti-logarithmic amplifier. U.S. Pat. No. 4,821,724 to Whigham et al. teaches the use of a triphasic stimulus having two positive pulses and one negative pulse for balancing the charge at the electrode/tissue interface.

U.S. Pat. No. 4,686,988 to Sholder teaches the use of a separate sensing electrode connected to a detector for detecting P-waves in the presence of atrial stimulation pulses, wherein the P-wave detector has an input bandpass characteristic selected to pass frequencies that are associated with P-waves. U.S. Pat. No. 4,858,610 to Callaghan et al. teaches the use of charge dumping following delivery of the stimulation pulse to decrease lead polarization and also the use of separate pacing and sensing electrodes to eliminate the polarization problem on the sensing electrode. The techniques of the '610 patent and '988 patent, which involve using a separate electrode located at some distance from the stimulating electrode for the purpose of isolating the polarization voltages or "afterpotential," are not completely desirable in that they require the additional cost and complexity of the additional sensing electrode.

U.S. Pat. No. 5,324,310 to Greeninger et al. teaches the use of the "ring-to-ring" sensing with corresponding atrial and ventricular EGM amplifiers whose outputs are multiplied and compared to a predetermined threshold to determine capture. U.S. Pat. No. 5,486,201 to Canfield discloses an active discharge circuit having a switching device which sequentially and repeatedly couples a charge transfer capacitor to the coupling capacitor to transfer charge therebetween and thereby actively discharge the coupling capacitor. None of these devices reduce or shorten the pacing afterpotentials through the use of a simplified pacing output. The present invention addresses these and other needs that will become apparent to those skilled in the art.

SUMMARY OF THE INVENTION

In accordance with a broad aspect of the present invention, the purpose of the present invention is to provide an improved pacing output and sensing circuits of a cardiac pacemaker, wherein the pacing circuit shortens pacing afterpotentials without significantly increasing the leading edge voltage pacing threshold. The pacing output circuit includes a power supply means, first capacitor means, first switching means, and afterpotential attenuation second capacitor means. The first capacitor means is cooperatively operable with the power supply means for selectively storing a pacing energy to be delivered to myocardial tissue in a heart via an electrode. The first switching means is provided for selectively delivering the pacing charge from the first capacitor means to the myocardial tissue within the heart. The second capacitor means is coupled to the electrode and cooperatively operable with the first capacitor means for attenuating pacing afterpotentials and blocking DC components from the heart. The second capacitor means preferably has a capacitance less than 5 microfarads.

The sensing circuit includes pace blanking switches, passive filters, sense amplifier, sense amplifier blanking switches, preamplifier, band pass filter, analog to digital converter and detection comparator. Both the pacing circuit and sensing circuit are operatively coupled to a microprocessor based controller. The pacing circuit shortens the pacing afterpotentials which allows the sensing circuit to incorporate switches controlled by the microprocessor based controller to thereby share sensing amplifier for sensing an evoked response and intrinsic events at two or more electrodes. The shortened pacing afterpotential further allows a reduced sense amplifier blanking time, which further enhances the ability to detect an evoked response.

OBJECTS

It is accordingly a principal object of the present invention to provide a low power consumption cardiac rhythm management device that attenuates polarization voltages or "afterpotentials" at the sensing electrode such that the evoked cardiac response to pacing stimulus may be readily detected.

Another object of the present invention is to provide an improved cardiac pacemaker which shortens the pacing afterpotentials with minimal increase of leading edge voltage pacing threshold.

Yet another object of the present invention is to provide an improved cardiac pacemaker that shortens the pacing afterpotentials and allows pacing and sensing of evoked response from the same electrodes.

Still another object of the present invention is to provide an improved cardiac pacemaker that shortens the pacing afterpotentials and allows a reduction in capacitance recharge time.

A further object of the present invention is to provide an improved cardiac pacemaker that shortens the pacing afterpotentials and allows for a reduced blanking period.

Without limitation, these and other objects as well as these and other advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE PREFERRED EMBODIMENT

Figure 1:
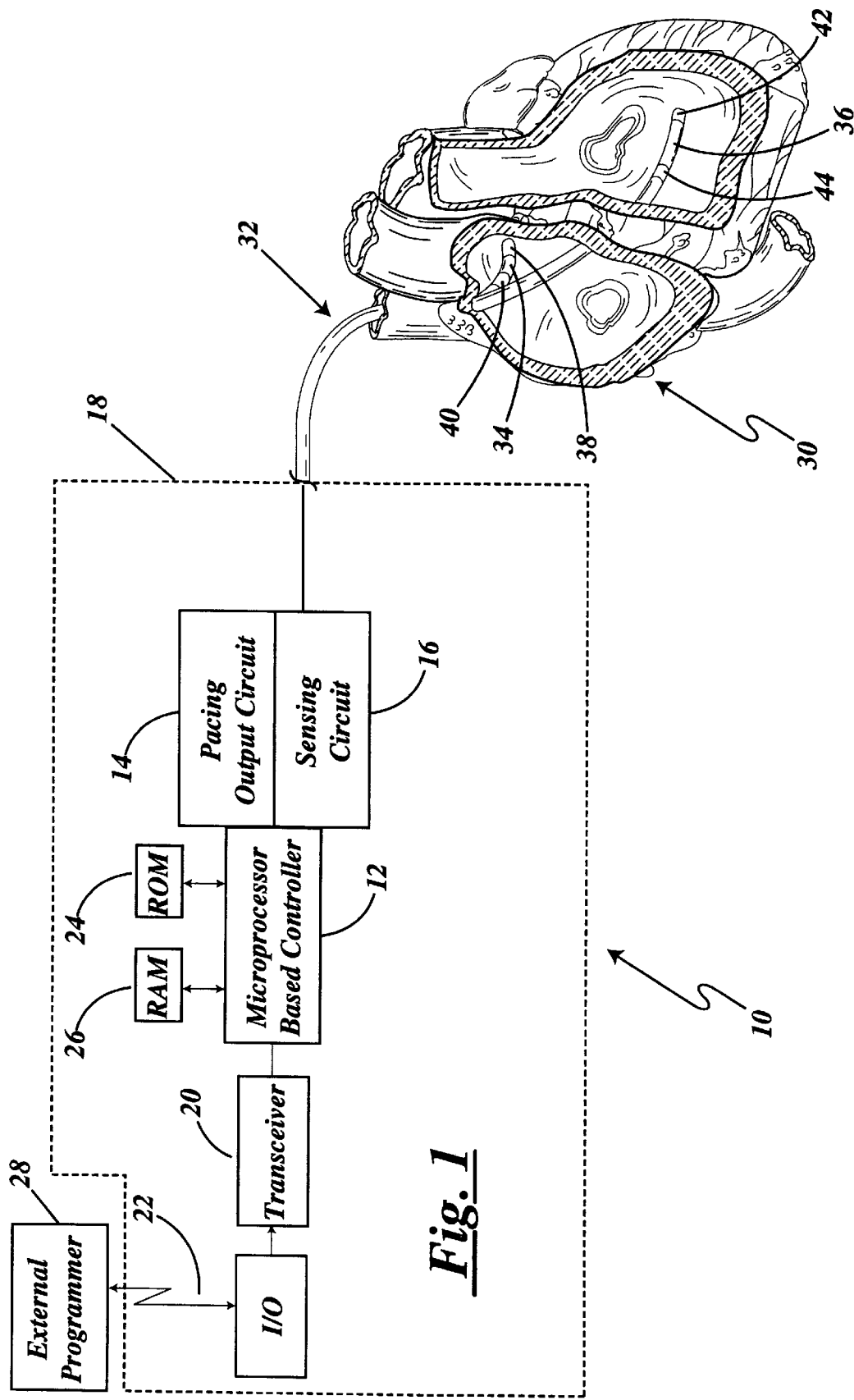
FIG. 1 is block diagram depicting a cardiac pacemaker incorporating the improved pacing circuitry for automatic capture threshold detection in accordance with the present invention.

In conjunction with the several views of the figures, details of a representative embodiment of a cardiac rhythm management device incorporating the features of the present invention will next be presented. Although the present invention may find application in a variety of implantable or external cardiac rhythm management devices, including but not limited to bradycardia pacemakers, antitachycardia pacemakers, and defibrillators, for purposes of explanation the present invention will be described in connection with an implantable rate adaptive cardiac pacemaker 10 as illustrated in FIG. 1. By way of illustration and not limitation, the cardiac pacemaker 10 is shown as a dual chamber (DDD) pacer having a microprocessor-based controller 12 including a pacing output circuit 14 and sensing circuit 16. The components of the cardiac pacemaker 10 are enclosed in a hermetically sealed housing represented schematically at 18. The microprocessor based controller 12 is operatively coupled to a transceiver 20 and input/output module 22. The cardiac pacemaker 10 also includes read-only memory (ROM) 24 and random access memory (RAM) 26 communicatively coupled to the microprocessor controller 12. The transceiver 20 is cooperatively operable with the input/output module 22 for transmitting and receiving information to and from an external programmer 28.

The cardiac pacemaker 10 is operatively coupled to a patient's heart 30 via a main pacing lead 32 which branches off into an atrial lead 34 and a ventricular lead 36. Bipolar pacing is possible utilizing the tip electrode 38 and ring electrode 40 of the atrial lead 34, or the tip electrode 42 and a ring electrode 44 of the ventricular lead 36. The microprocessor based controller 12 is independently electrically coupled via electrical conductors (not shown) to each of the electrodes 38–44. As will be further discussed below, each of the electrodes 38–44 may be utilized for either unipolar or bipolar pacing and ring electrodes 40 and 44 may be utilized for both pacing and sensing.

Figure 2:
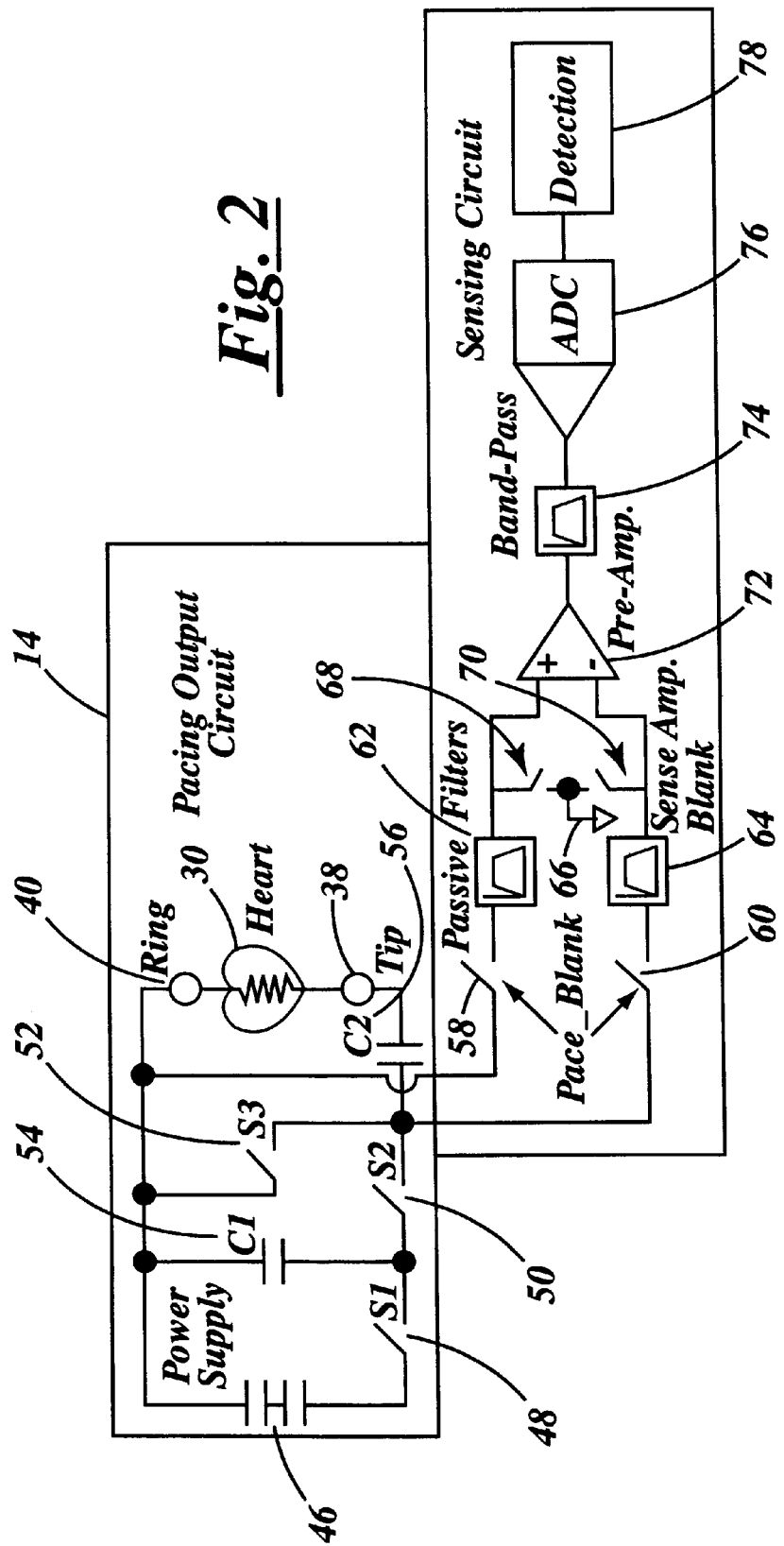
FIG. 2 is a schematic of an improved pacing output circuit and sensing circuit provided in accordance with a preferred embodiment of the present invention.

Referring now to FIG. 2, the components of the pacing output circuit 14 and sensing circuit 16 are shown in greater detail. Although the pacing output circuit 14 is shown only for the atrial lead 34, those skilled in the art will appreciate that a similar pacing and sensing circuitry may be utilized for ventricular sensing and pacing. As will be explained below, the improved pacing output circuit 14 is capable of quickly attenuating any polarization voltages or "afterpotentials" which result due to the application of stimulus pulses to the heart 30. By attenuating the polarization voltages or "afterpotentials" in this fashion, the improved pacing circuit 14 and sensing circuit 16 of the present invention facilitates the task of capture verification in that the presence or absence of evoked responses may be readily determined without the masking caused by afterpotentials. Capture verification advantageously allows the pacemaker 10 to automatically adjust the pacing output parameters so as to minimize power consumption while assuring therapeutic efficacy.

In a preferred embodiment, the improved pacing output circuit 14 of the present invention includes a power supply or battery, a first switch (S1) 48, a second switch (S2) 50, a third switch (S3) 52, a pacing charge storage capacitor (C1) 54, and an afterpotential reduction capacitor/coupling capacitor (C2) 56, all of which are cooperatively operable under the direction of the microprocessor-based controller 12 shown in FIG. 1. The power supply or battery 46 is preferably the battery provided to power the pacemaker 10 and may comprise any number of commercially available batteries suitable for pacing applications. The switches 48–52 are preferably carried out via any number of conventionally available microprocessor-directed semiconductor integrated circuit switching means. The pacing charge storage capacitor 54 may also comprise any number of conventional storage capacitors, but is preferably provided with a capacitance in the range of 10–30 microfarads so as to develop a sufficient pacing charge for stimulating the heart 30. The primary function of the coupling capacitor 56 is to quickly attenuate the polarization voltage or "afterpotentials" which result from pacing and additionally block any DC signals from reaching the heart 30 during pacing. The coupling capacitor 56 has a capacitance in the range less than 5 microfarads, with a 2.2 microfarad capacitor being preferred.

The sensing circuit 16 includes pace blanking switches 58 and 60, passive filters 62 and 64, voltage reference 66, sense amplifier blanking switches 68 and 70, preamplifier 72, band pass filter 74, analog to digital converter 76 and detection comparator 78. The micro-processor based controller 12 is operatively coupled to the sensing circuit 16 and controls the opening and closing of switches 58, 60, 68, and 70. Although switches 58, 60, 68, and 70 are illustrated as discrete components, those skilled in the art will appreciate that they may comprise any number of commercially available microprocessor-directed semiconductor integrated circuit switching means. The pace blanking switches 58 and 60 are closed independently to detect an evoked response from the corresponding pacing electrode, and the shortening of the pacing afterpotentials by using a reduced capacitance coupling capacitor allows pacing and sensing of the evoked response from the same electrodes. The intrinsic sensing channel may also be shared for efficient system operation. By shortening the pacing afterpotentials, the recharge time of the coupling capacitor 56 may be reduced from a conventional time of greater than 20 milliseconds to under 10 milliseconds. This shortened time usually lapses before the onset of an evoked response. In turn, the sense amplifier blanking time may be reduced from a conventional 30 milliseconds to under 15 milliseconds with 12 milliseconds being preferred. This shortened blanking period in conjunction with the shortening of the pacing afterpotentials increases the likelihood of detecting an evoked response.

Having described the constructional features of the present invention the mode of use will next be described in greater detail. The microprocessor based controller 12 implements pre-programmed sequence to control the charging cycle, pacing cycle, and recharge cycle of the pacing output circuit 14. The charging cycle is characterized as having the first switch 48 in a closed state with the second switch 50 and third switch 52 in an open state. In this configuration, the pacing charge storage capacitor 54 may be charged up to a predetermined pacing voltage level, such as 3 volts. After the pacing charge storage capacitor 54 has been charged up to the predetermined pacing voltage level, the pacing cycle then operates to deliver the pacing charge from the pacing charge storage capacitor 54 to the heart 30.

To accomplish the pacing cycle, the first switch 48 is opened and third switch 52 remains opened and the second switch 50 is closed. This allows the voltage within the pacing charge storage capacitor 54 to be discharged through the coupling capacitor 56 to the tip electrode 38 positioned in the heart 30. The coupling capacitor 56 is less than 5 microfarads. This, once again, effectively blocks any significant DC signals from reaching the heart 48, while shortening the pacing afterpotentials.

The recharge cycle involves keeping open the first switch 48 and opening the second switch 50 while closing the third switch 52. This allows the circuit 14 to passively recharge, such that the charge within the heart 30 is allowed to flow back into the circuit 14 to balance out. During this passive recharge period, the charge on the coupling capacitor 56 is such that the signal decays over a short period of time and less than required blanking period preceding detection of any evoked response from the heart 30. This is because the evoked responses from the heart 30 typically begins within 20 milliseconds from the delivery of the stimulus pulse, which is substantially longer than the required recharge time. Advantageously, it has been found that reducing the overall capacitance of the coupling capacitor 56 quickly attenuates the polarization voltages or "afterpotentials" which result immediately following the application of a stimulus pulse such that the evoked responses within the heart 30 will not be masked or buried within the "afterpotential." By eliminating the adverse affects of "afterpotentials" in this fashion, the pacemaker 10 can easily sense an evoked response and track the capture threshold of the heart 30 over time. Those skilled in the art will appreciate that with the continuous knowledge of the capture threshold in hand, the pacemaker 10 may be automatically adjusted to maintain an optimal pacing stimulus level which ensures safe pacing while minimizing power consumption.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An improved pacing output circuit for use in implantable and external cardiac rhythm management device, said pacing output circuit comprising:
    (a) power supply means;
    (b) first capacitor means cooperatively operable with said power supply means for selectively storing a pacing charge to be delivered to myocardial tissue in a heart via an electrode;
    (c) first switching means electrically coupled to said first capacitor means for selectively delivering said pacing charge from said first capacitor means to said myocardial tissue within said heart;
    (d) second capacitor means electrically coupled to said first switching means and said electrode for coupling said first capacitor means with said electrode, said second capacitor means having a capacitance less than 5 microfarads.

2. The improved pacing output circuit as set forth in claim 1 and further including a sensing circuit that shares a sense amplifier between two or more pacing electrodes.

3. The improved pacing output circuit as set forth in claim 2 and further, said first switching means including a first switch for selectively coupling said power supply means to said first capacitor means for developing said pacing energy within said first capacitor means and a second switch for selectively coupling said first capacitor means to said second capacitor means for discharging said pacing charge from said first capacitor means into said heart via said electrode.

4. The improved pacing output circuit as set forth in claim 3 and further, said first capacitor means having a capacitance greater than 5 microfarads.

5. An improved method for attenuating afterpotentials in cardiac pacing systems, comprising the steps of:
    (a) providing a pacing output circuit, said pacing output circuit having means for selectively delivering a stimulating pulse to an electrode disposed within a chamber of a patient's heart and a coupling capacitor coupled to said means for selectively delivering and said electrode for shortening pacing afterpotentials and blocking significant DC components from entering said patient's heart; and
    (b) maintaining the capacitance of said coupling capacitor at a capacitance less than 5 microfarads.

6. An improved cardiac pacemaker, comprising:
    pulse generation means for selectively generating stimulus pulses;
    lead means coupled to said pulse generation means and adapted to deliver said stimulus pulses to a patient's heart;
    said pulse generation means including power supply means, first capacitor means cooperatively operable with said power supply means for selectively storing a pacing charge to be delivered to said heart via said lead means, first switching means electrically coupled to said first capacitor means for selectively delivering said pacing charge from said first capacitor means to said heart via said lead means, second capacitor means coupled to said lead means and cooperatively coupled and operable with said first capacitor means for attenuating the pacing afterpotentials and blocking DC components from said heart during pacing which result due to the application of said pacing charge to said heart, wherein said second capacitor means having a capacitance less than 5 microfarads.

7. The improved cardiac pacemaker as set forth in claim 6 and further, said second capacitor means having a substantially smaller capacitance than said first capacitor means.

8. The improved cardiac pacemaker as set forth in claim 7 and further, said first switching means including a first switch for selectively coupling said power supply means to said first capacitor means for developing said pacing charge within said first capacitor means and a second switch for selectively coupling said first capacitor means to said second capacitor means for discharging said pacing charge from said first capacitor means into said heart via said electrode.

9. The improved cardiac pacemaker as set forth in claim 8 and further, said first capacitor means having a capacitance greater than 5 microfarads.

10. The improved cardiac pacemaker as recited in claim 6, wherein recharge time for the second capacitor means is reduced to under 15 milliseconds.

11. The improved cardiac pacemaker as recited in claim 6, further including a sensing means for sensing an evoked response of the heart, wherein said sensing means has a sense amplifier blanking time ranging between 8 to 15 milliseconds.

12. The improved cardiac pacemaker as recited in claim 6, further including a sensing circuit that shares a sense amplifier between two or more pacing electrodes.

* * * * *